United States Patent [19]
Rentzea et al.

[11] Patent Number: 5,326,743
[45] Date of Patent: Jul. 5, 1994

[54] PIPERAZINE-2,3-DIONES AS PLANT GROWTH REGULATORS

[75] Inventors: Costin Rentzea, Heidelberg; Albrecht Harreus, Ludwigshafen; Andreas Landes, Limburgerhof; Helmut Walter, Obrigheim; Wilhelm Rademacher, Limburgerhof, all of Fed. Rep. of Germany

[73] Assignee: BASF Aktiengesellschaft, Ludwigshafen, Fed. Rep. of Germany

[21] Appl. No.: 102,743

[22] Filed: Aug. 6, 1993

[30] Foreign Application Priority Data

Aug. 11, 1992 [DE] Fed. Rep. of Germany ....... 4226558

[51] Int. Cl.$^5$ .................... A01N 43/60; C07D 241/08
[52] U.S. Cl. .................... 504/235; 544/383
[58] Field of Search ............ 544/383; 504/235; A01N 43/60

[56] References Cited

U.S. PATENT DOCUMENTS 4,057,413 11/1977 Naumann et al. .................... 71/76

FOREIGN PATENT DOCUMENTS 469423 2/1992 European Pat. Off. .

OTHER PUBLICATIONS

Schmidt et al., "1,3-Dihydroxyharstoffe, 2.Mitt", *Archiv der Pharmazie*, vol. 312, No. 12, 1979, pp. 1019–1026.

Chem. Abst., vol. 111, No. 19, Nov. 6, 1989 (abst. of CS-B 256 558). 169382x.

Chem. Abst., vol. 72, no. 1, Jan. 5, 1970 (abst. of DE-A 901421). 3053s.

Chem. Abst., vol. 70, No. 5, Feb. 3, 1969 (abst. of JP 68 17 962). 20066z.

Chem. Ber 27 (1894), 1111; DE 40 24 283.

*Primary Examiner*—Cecilia Tsang
*Attorney, Agent, or Firm*—Keil & Weinkauf

[57] ABSTRACT

Piperazine-2,3-diones of the formula I

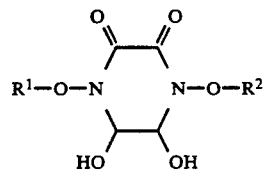

where $R^1$ and $R^2$ are identical or different and each is alkyl, alkenyl or alkynyl, where these groups may carry from one to five halogen atoms;

monocyclic or polycyclic cycloalkyl, cycloalkenyl, cycloalkylmethyl or cycloalkenylmethyl, where the rings may carry from one to three alkyl groups or a phenyl ring; or phenyl, phenylalkyl or phenylalkenyl, where the aromatic radicals may carry from one to five halogen atoms and/or from one to three of the following groups: nitro, alkyl, haloalkyl, alkoxy, haloalkoxy, alkylthio or haloalkylthio, methods for their manufacture, agents containing them and the use thereof.

10 Claims, No Drawings

PIPERAZINE-2,3-DIONES AS PLANT GROWTH REGULATORS

The present invention relates to piperazine-2,3-diones of the formula I

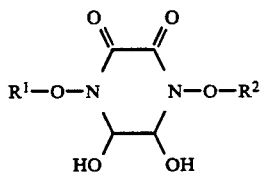

where $R^1$ and $R^2$ independently of one another are each $C_1$–$C_{20}$-alkyl, $C_3$–$C_{18}$-alkenyl or $C_3$–$C_8$-alkynyl, where these groups may carry from one to five halogen atoms, monocyclic or polycyclic $C_3$–$C_{10}$-cycloalkyl, $C_5$–$C_{10}$-cycloalkenyl, $C_3$–$C_{10}$-cycloalkylmethyl or $C_5$–$C_{10}$-cycloalkenylmethyl, where the rings may carry from one to three $C_1$–$C_4$-alkyl groups or a phenyl ring, or phenyl, phenyl-$C_1$–$C_4$-alkyl or phenyl-$C_2$–$C_6$-alkenyl, where the aromatic radicals may carry from one to five halogen atoms and/or from one to three of the following groups: nitro, $C_1$–$C_4$-alkyl, $C_1$–$C_4$-naloalkyl, $C_1$–$C_4$-alkoxy, $C_1$–$C_4$-haloalkoxy, $C_1$–$C_4$-alkylthio or $C_1$–$C_4$-haloalkylthio.

The present invention furthermore relates to processes for the preparation of these compounds, agents containing them and methods for their use as plant growth regulators.

It is an object of the present invention to provide novel effective plant growth regulators.

We have found that this object is achieved by the piperazine-2,3-diones I defined at the outset. We have also found processes for the preparation of these compounds, agents containing them and methods for their use as plant growth regulators.

The piperazine-2,3-diones of the formula I are obtained, for example, by reacting an oxalylbishydroxamic acid derivative of the formula II, in a conventional manner in an organic solvent or in water, with anhydrous glyoxal or with an aqueous solution thereof, in the presence or absence of an inorganic or organic base and of a catalyst.

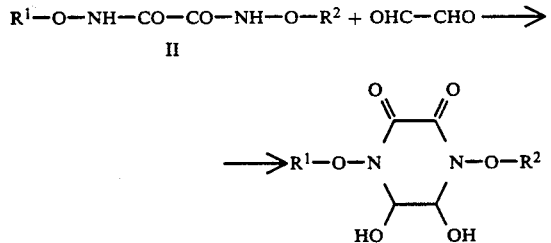

The reaction is carried out in general at from 0° to 100° C., preferably from 20° to 80° C.

Examples of suitable solvents are alcohols, such as methanol, ethanol, propanol, isopropanol and butanol, ethers, such as ethylene glycol dimethyl ether, tetrahydrofuran and dioxane, nitriles, such as acetonitrile and propionitrile, amides, such as dimethylformamide, dimethylacetamide and N-methylpyrrolidone, acids, such as acetic acid and propionic acid, if required also water and corresponding mixtures. Advantageously, the solvent is used in an amount of from 100 to 2,000, preferably from 200 to 700, % by weight, based on the starting material II.

The preparation of the oxalylbishydroxamic acid derivatives II is known from the literature (Chem. Ber. 27 (1894), 1111;DE-A 40 24 283).

Examples of suitable bases and/or catalysts are potassium hydroxide, sodium hydroxide, potassium carbonate, sodiumcarbonate, lithiumhydroxide, lithiumcarbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc hydroxide, sodium formate, sodium acetate, trimethylamine, triethylamine, tripropylamine, triisopropylamine, tributylamine, triisobutylamine, tribenzylamine, tricyclohexylamine, triamylamine, trihexylamine, N,N-dimethylaniline, N,N-diethylaniline, N,N-dipropylaniline, N,N-dimethyltoluidene, N,N-diethyltoluidene, N,N-dipropyltoluidene, N,N-dimethyl-4-aminopyridine, N,N-diethyl-4-aminopyridine, N,N-dipropyl-4-aminopyridine, N,N-dipropyl-4-aminopyridine, N-methylpiperidine, N-ethylpiperidine, N-methylpyrrolidine, N-ethylpyrrolidine, N-methylimidazole, N-ethylimidazole, N-methylmorpholine, N-ethylmorpholine, N-methylhexamethyleneimine, N-ethylhexamethyleneimine, pyridine, quinoline, alphapicoline, betapicoline, isoquinoline, N,N,N',N'-tetramethylethylenediamine, N,N,N',N'-tetraethylethylenediamine, N-propyldiisopropylamine, N,N-dimethylcyclohexylamine, 2,6-lutidine, 2,4-lutidine and triethylenediamine.

Advantageously, the base is used in amounts of from 1 to 20 mol %, based on the starting material II.

In view of the intended use of the compounds I and growth regulators containing them, suitable substituents are the following radicals:

$R^1$ and $R^2$ independently of one another are each $C_1$–$C_{20}$-alkyl, preferably branched or straight-chain $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular branched or straight-chain $C_1$–$C_4$-alkyl, such as methyl, ethyl, propyl, 1-methylethyl, butyl, 1-methylpropyl, 2-methylpropyl or 1,1-dimethylethyl, $C_3$–$C_{18}$-alkenyl, in particular $C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2- butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3 -butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, or $C_3$–$C_8$-alkynyl, in particular $C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 2-methyl-3-butynyl, 1,1-dimethyl-2-propynyl, 1-ethyl-2-propynyl, 2-hexynyl, 3-hexynyl, 4hexynyl, 5-hexynyl, 1-methyl-2-pentynyl, 1-methyl-3pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl or 2-butynyl, where these groups may carry from one to five halogen atoms, such as fluorine, chlorine, bromine or iodine, preferably fluorine or chlorine, monocyclic or polycyclic $C_3$–$C_{10}$-cycloalkyl, such as cyclopropyl, cyclobutyl, cyclopentyl, cyclohexyl, cycloheptyl, cyclooctyl, menthyl, norbornyl, adamantyl or tricyclodecanyl, preferably cyclopropyl or cyclohexyl, or monocyclic or polycyclic $C_5$–$C_{10}$-cycloalkenyl, preferably 2-cyclohexen-1-yl, monocyclic or polycyclic $C_3$–$C_{10}$-cycloalkylmethyl, such as cyclopropylmethyl, cyclobutylmethyl, cyclopentylmethyl, cyclohexylmethyl, cycloheptylmethyl or cyclooctylmethyl, preferably cyclopropylmethyl or cyclohexylmethyl, or monocyclic or polycyclic $C_5$–$C_{10}$-cycloalkenylmethyl, preferably 1-cyclohexenylmethyl, 2-cyclohexenylmethyl or 3-cyclohexenylmethyl, where the rings may carry from one to three $C_1$–$C_4$-alkyl groups, such as methyl, ethyl, propyl, 1-methylethyl, butyl, 1-methylpropyl, 2-methylpropyl or 1,1-dimethylethyl, preferably methyl or ethyl, in particular methyl, or a phenyl ring, phenyl, phenyl-$C_1$–$C_4$-alkyl, such as benzyl, 1-phenylethyl, 2-phenylethyl, 1-phenylpropyl, 2-phenylpropyl, 3-phenylpropyl, 1-methyl-1-phenylethyl, 1-methyl-2-phenylethyl, 1-phenylbutyl, 2-phenylbutyl, 3-phenylbutyl, 4-phenylbutyl, 1-methyl-1-phenylpropyl, 1-methyl-2-phenylpropyl, 1-methyl-3-phenylpropyl, 2-methyl-1-phenylpropyl, 2-methyl-2-phenylpropyl, 2-methyl-3-phenylpropyl or 1,1-dimethyl-2-phenylethyl, preferably benzyl or 2-phenylethyl, or phenyl-$C_2$–$C_6$-alkenyl, in particular phenyl-$C_2$–$C_4$-alkenyl, such as 2-phenylethenyl, 2-phenyl-1-propenyl, 2-phenyl-2-propenyl, 2-phenyl-1-methylethenyl, 2-phenyl-1-butenyl, 2-phenyl-2-butenyl, 2-phenyl-3-butenyl, 2-phenyl-1-methyl-1-propenyl or 2-phenyl-1-methyl-2-propenyl, where the aromatic radicals may carry from one to five halogen atoms, such as fluorine, chlorine, bromine or iodine, preferably fluorine, chlorine or bromine, in particular fluorine or chlorine, and/or from one to three of the following groups: nitro, $C_1$–$C_4$-alkyl, such as methyl, ethyl, propyl, 1-methylethyl, butyl, 1-methylpropyl, 2-methylpropyl or 1,1-dimethylethyl, preferably methyl, 1-methylethyl or 1,1-dimethylethyl, $C_1$–$C_4$-haloalkyl, preferably $C_1$- or $C_2$-haloalkyl, such as chloromethyl, dichloromethyl, trichloromethyl, fluoromethyl difluoromethyl, trifluoromethyl, chlorofluoromethyl dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl, $C_1$–$C_4$-alkoxy, such as methoxy, ethoxy, propoxy, 1-methylethoxy, butoxy, 1 -methylpropoxy, 2 -methylpropoxy or 1,1-dimethylethoxy, preferably methoxy or ethoxy, $C_1$–$C_4$-haloalkoxy, in particular $C_1$- or $C_2$-haloalkoxy, such as chloromethoxy, dichloromethoxy, trichloromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio butylthio, 1-methylpropylthio, 2-methylpropylthio or 1,1-dimethylethylthio, preferably methylthio, and $C_1$–$C_4$-haloalkylthio, in particular $C_1$- or $C_2$-haloalkylthio, such as chloromethylthio, dichloromethylthio, trichloromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio.

In view of the intended use in growth regulators, particularly preferred compounds I are those in which $R^1$ is methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethyldimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl, propyl, 1-methylethyl, butyl, 1-methylpropyl, 2-methylpropyl or 1,1-dimethylethyl, 2-propenyl, 2-butenyl, 3-butenyl, 1-methyl-2-propenyl, 2-methyl-2-propenyl, 3-methyl-2-butenyl or benzyl, where these groups may carry from one to five halogen atoms, such as fluorine, chlorine, bromine or iodine, preferably fluorine or chlorine.

Examples of particularly preferred piperazine-2,3-diones of the formula I are shown in the Table below.

TABLE A

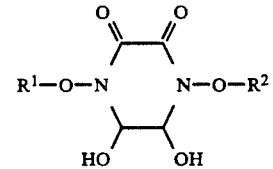

I

| $R^1$ | $R^2$ |
|---|---|
| CH$_3$ | CH$_3$ |
| CH$_3$ | C$_2$H$_5$ |
| CH$_3$ | n-C$_3$H$_7$ |
| CH$_3$ | i-C$_3$H$_7$ |
| CH$_3$ | n-C$_4$H$_9$ |
| CH$_3$ | i-C$_4$H$_9$ |
| CH$_3$ | sek.-C$_4$H$_9$ |
| CH$_3$ | n-C$_5$H$_{11}$ |

TABLE A-continued $$R^1-O-N \begin{array}{c} O \\ \parallel \\ \diagdown \end{array} \begin{array}{c} O \\ \parallel \\ \diagup \end{array} N-O-R^2$$
$$\phantom{R^1-O-N} HO \quad OH \qquad \qquad I$$

| $R^1$ | $R^2$ |
|---|---|
| $CH_3$ | i-$C_5H_{11}$ |
| $CH_3$ | n-$C_6H_{13}$ |
| $CH_3$ | $(CH_3)_2CHCH_2CH_2CH_2$ |
| $CH_3$ | n-$C_7H_{15}$ |
| $CH_3$ | n-$C_8H_{17}$ |
| $CH_3$ | $CH_3CH_2CH_2CH_2CH(C_2H_5)CH_2$ |
| $CH_3$ | n-$C_9H_{19}$ |
| $CH_3$ | n-$C_{10}H_{21}$ |
| $CH_3$ | n-$C_{12}H_{25}$ |
| $CH_3$ | n-$C_{14}H_{29}$ |
| $CH_3$ | n-$C_{16}H_{33}$ |
| $CH_3$ | n-$C_{18}H_{37}$ |
| $CH_3$ | n-$C_{20}H_{41}$ |
| $CH_3$ | Cyclopropylmethyl |
| $CH_3$ | Cyclopentyl |
| $CH_3$ | Cyclohexyl |
| $CH_3$ | Cyclohexylmethyl |
| $CH_3$ | 4-Methylcyclohexyl |
| $CH_3$ | 4-Ethylcyclohexyl |
| $CH_3$ | 4-tert.-Butylcyclohexyl |
| $CH_3$ | Allyl |
| $CH_3$ | $CH_3CH=CHCH_2$ |
| $CH_3$ | $(CH_3)_2C=CHCH_2$ |
| $CH_3$ | Geranyl |
| $CH_3$ | $HC\equiv CCH_2$ |
| $CH_3$ | $CH_3C\equiv CCH_2$ |
| $CH_3$ | $ClCH_2=CHCH_2$ |
| $CH_3$ | $CH_2=C(Cl)CH_2$ |
| $CH_3$ | $CH_2=C(Br)CH_2$ |
| $CH_3$ | $ClCH=C(Cl)CH_2$ |
| $CH_3$ | $Cl_2=C(Cl)CH_2$ |
| $CH_3$ | $ClCH_2CH_2$ |
| $CH_3$ | $Cl_3CCH_2$ |
| $CH_3$ | $ClCH_2CH_2CH_2$ |
| $CH_3$ | $Cl(CH_2)_4$ |
| $CH_3$ | $BrCH_2CH_2$ |
| $CH_3$ | $Cl-(CH_2)_6$ |
| $CH_3$ | $Cl-(CH_2)_8$ |
| $CH_3$ | $Br-(CH_2)_4$ |
| $CH_3$ | $Br-(CH_2)_6$ |
| $CH_3$ | $C_6H_5-CH_2$ |
| $CH_3$ | $4Cl-C_6H_4-CH_2$ |
| $CH_3$ | $3Cl-C_6H_4-CH_2$ |
| $CH_3$ | $3,4Cl_2-C_6H_3-CH_2$ |
| $CH_3$ | $2,4Cl_2-C_6H_3-CH_2$ |
| $CH_3$ | $4-F-C_6H_4-CH_2$ |
| $CH_3$ | $4-Br-C_6H_4-CH_2$ |
| $CH_3$ | $4-CH_3-C_6H_4-CH_2$ |
| $CH_3$ | $2,4-(CH_3)_2-C_6H_3-CH_2$ |
| $CH_3$ | $4-C_2H_5-C_6H_4-CH_2$ |
| $CH_3$ | $4-i-C_3H_7-C_6H_4-CH_2$ |
| $CH_3$ | $4-tert.-C_4H_9-C_6H_4-CH_2$ |
| $CH_3$ | $4-CH_3O-C_6H_4-CH_2$ |
| $CH_3$ | $4-O_2N-C_6H_4-CH_2$ |
| $CH_3$ | $C_6H_5-CH_2CH_2$ |
| $C_2H_5$ | $C_2H_5$ |
| $C_2H_5$ | n-$C_3H_9$ |
| $C_2H_5$ | i-$C_3H_9$ |
| $C_2H_5$ | n-$C_4H_9$ |
| $C_2H_5$ | sek.-$C_4H_9$ |
| $C_2H_5$ | i-$C_4H_9$ |
| $C_2H_5$ | $H_2C=C(CH_3)-CH_2$ |
| i-$C_3H_7$ | i-$C_3H_7$ |
| Allyl | Allyl |
| $H_2C=CClCH_2$ | $H_2C=CClCH_2$ |
| $H_2C=CBrCH_2$ | $H_2C=CBrCH_2$ |
| $ClCH=CHCH_2$ | $ClCH=CHCH_2$ |
| $CH_3CH=CHCH_2$ | $CH_3CH=CHCH_2$ |
| $H_2C=C(CH_3)CH_2$ | $H_2C=C(CH_3)CH_2$ |
| $ClCH_2CH_2CH_2$ | $ClCH_2CH_2CH_2$ |
| n-$C_4H_9$ | n-$C_4H_9$ |
| i-$C_4H_9$ | i-$C_4H_9$ |
| sek.-$C_4H_9$ | sek.-$C_4H_9$ |
| n-$C_5H_{11}$ | n-$C_5H_{11}$ |
| n-$C_6H_{13}$ | n-$C_6H_{13}$ |
| $HC\equiv CCH_2$ | $HC\equiv CCH_2$ |
| $C_6H_5-CH_2$ | $C_6H_5-CH_2$ |

The growth-regulating active ingredients I according to the invention, or agents containig them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The active ingredients I are generally suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone and water.

Aqueous formulations may be prepared from emulsion concentrates, pastes, oil dispersions, wettable powders or waterdispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycot ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.5 to 90, % by weight of active ingredient. The active ingredients are used in a purity of from 90 to 100, and preferably from 95 to 100, % (according to the NMR spectrum). Examples of formulations are as follows:

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 2 is dissolved in a mixture consisting of 25 parts by weight of cyclohexanone, 65 parts by weight of a mineral oil fraction having a boiling point between 210° and 280° C., and 10 parts by weight Of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3 is intimately mixed with 97 parts by weight of particulate kaolin. A dust is obtained containing 3% by weight of the active ingredient.

VII. 30 parts by weight of compound no. 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 4 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 90 parts by weight of compound no. 4 is mixed with 10 parts by weight of N-methyl-α-pyrrolidone. A mixture is obtained which is suitable for application in the form of very fine drops.

X. 20 parts by weight of compound no. 4 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

XI. 20 parts by weight of compound no. 6 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

XII. 20 parts by weight of compound no. 7 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

XIII. 20 parts by weight of compound no. 6 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

XIV. 3 parts by weight of compound no. 5 is intimately mixed with 97 parts by weight of particulate kaolin. A dust is obtained containing 3% by weight of the active ingredient.

XV. 30 parts by weight of compound no. 6 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

XVI. 20 parts by weight of compound no. 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The application rates depend on the time of the year, the plants to be combated and their growth stage, and are from 0.01 to 5.0, preferably 0.05 to 2, kg of active ingredient per hectare.

The compounds of the formula IA may exercise a variety of influences on practically all plant development stages, and are therefore used as growth regulators. The diversity of action of growth regulators depends especially on
a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitation, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

In fruit and other trees, pruning costs can be reduced with growth regulators. With growth regulators, it is also possible to break up the alternate breeding rhythm of fruit trees.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and because of the relatively low leaf or plant mass - attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia,
the size of the stomata opening is reduced;
a thicker epidermis and cuticle are formed;
penetration of the soil by the roots is improved;
the micro-climate in the stand is favorably influenced by the more compact growth.

The active ingredients to be employed according to the invention may be applied not only to the seed (as a dressing), but also to the soil, i.e., via the roots, and—the method particularly preferred—to the foliage by spraying.

In view of the numerous application methods possible, the compounds according to the invention, or agents containing them, may be used in a large number of crops.

To increase the spectrum of action and to achieve synergistic effects, the active ingredients IA according to the invention may be mixed and applied together with numerous representatives of growth-regulating active ingredient groups.

It may also be useful to apply the active ingredients I in combination with herbicides and/or other agents for combating pests or phytopathogenic fungi or bacteria. The active ingredients may also be mixed with solutions of mineral salts used to remedy nutritional or trace element deficiencies. Non-phytotoxic oils and oil concentrates may also be added.

SYNTHESIS EXAMPLES

The directions given in the synthesis examples below were employed, after appropriate modifications to the starting materials, to obtain further active ingredients I. The compounds thus obtained are listed with their physical data in the table below.

EXAMPLE 1

1,4-Bis (1-propenyl-3-oxy)-2,3-dioxo-5,6-dihydroxypiperazine 52.1 ml (0.36 mol) of a 40% strength aqueous glyoxal solution was added to a solution of 30 g (0.15 mol) of bis(1-propenyl-3-oxyamino)ethanedione in 170ml of ethanol, and the pH of the mixture was brought to 7 to 7.5 with 1N sodium hydroxide solution. After the mixture had been stirred for 72 hours at 25° C. it was evaporated down under reduced pressure. The residue was stirred for 30 minutes with 200 ml of ethyl acetate and then filtered, and the filtrate was freed from solvent under reduced pressure. The residue obtained was crystallized with 20 ml of ether and 0.5 ml of methanol at 0° C. There was obtained 12.1 g (31.2% of theory) of 1,4-bis(1-propenyl-3-oxy)-2,3-dioxo-5,6-dihydroxypiperazine as white crystals of m.p. 142°–144° C.

TABLE 1

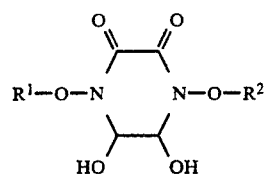

| Ex. no. | $R^1$ | $R^2$ | m.p. (°C.) |
|---|---|---|---|
| 1 | $CH_2=CHCH_2$ | $CH_2=CHCH_2$ | 142–144 |
| 2 | $CH_3$ | $CH_3$ | 198–201 |
| 3 | $i-C_3H_7$ | $i-C_3H_7$ | 195 |
| 4 | $n-C_4H_9$ | $n-C_4H_9$ | 114–117 |
| 5 | $n-C_5H_{11}$ | $n-C_5H_{11}$ | 124–126 |
| 6 | $CH_2=C(CH_3)CH_2$ | $CH_2=C(CH_3)CH_2$ | 171–174 |
| 7 | $HC\equiv CCH_2$ | $HC\equiv CCH_2$ | 186 |

USE EXAMPLES

To determine the growth-regulating properties of the candidate compounds, test plants were grown in plastic pots (approx. 8 cm in diameter and having a volume of approx. 300 ml) in a substrate provided with sufficient nutrients.

The candidate compounds were sprayed on to the plants as aqueous formulations. The growth-regulating action observed was confirmed at the end of the experiment by measuring the height of the plants. The figures obtained were compared with the growth height of the untreated plants.

The reduction in growth height was also accompanied by a deeper leaf coloration. The increased chlorophyll content is indicative of an increased rate of photosynthesis, making for bigger yields.

The prior art agent used for comparison purposes was CCC:

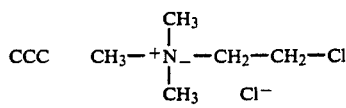

The test plants employed were *Brassica napus* (winter rape; abbreviation: BRSNW), *Hordeum vulgaris* (spring barley; abbreviation: HORVS) and *Triticum aestivum* (spring wheat; abbreviation: TRZAS). The results of the experiments are given in the following tables:

TABLE 2

| Substance | kg/ha | HORVS[a] | TRZAS[b] |
|---|---|---|---|
| Substance | —/— | 100 | 100 |
| CCC | 3 | 83 | 79 |
|  | 1.5 | 83 | 84 |
|  | 0.75 | 86 | 84 |
|  | 0.375 | 92 | 84 |
| No. 1 | 0.5 | 61 | 65 |
|  | 0.25 | 86 | 81 |
|  | 0.125 | 89 | 95 |
|  | 0.06 | 92 | 95 |
| No. 6 | 0.5 | 41 | 48 |
|  | 0.25 | 70 | 56 |
|  | 0.125 | 73 | 67 |
|  | 0.06 | 83 | 84 |
| No. 4 | 0.5 | 89 | 84 |
|  | 0.25 | 92 | 90 |
|  | 0.125 | 96 | 95 |

[a]"Alexis" variety
[b]"Star" variety

TABLE 3

| | kg/ha | BRSNW[a] |
|---|---|---|
| untreated | — | 100 |
| CCC | 3 | 75 |
|  | 1.5 | 85 |
|  | 0.75 | 85 |
|  | 0.375 | 96 |
| No. 6 | 0.5 | 64 |
|  | 0.25 | 75 |
|  | 0.125 | 85 |
|  | 0.06 | 85 |

[a]"Liberator" variety

We claim:
1. Piperazine-2,3-diones of the formula where $R^1$ and $R^2$ are identical or different and each is $C_1$–$C_{20}$-alkyl, $C_3$–$C_{18}$-alkenyl or $C_3$–$C_8$-alkynyl, where these groups may carry from one to five halogen atoms; $C_3$–$C_{10}$-cycloalkyl, $C_5$–$C_{10}$-cycloalkenyl, $C_3$–$C_{10}$-cycloalkylmethyl or $C_1$–$C_4$-cycloalkenylmethyl, where the rings may carry from one to three $C_1$–$C_4$-alkyl groups or a phenyl ring or norbonyl, adamantyl or tricyclodecamyl; or phenyl, phenyl-$C_1$–$C_4$-alkyl or phenyl-$C_2$–$C_6$-alkenyl, where the aromatic radicals may carry from one to five halogen atoms and/or from one to three of the following groups; nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio.

2. A composition for regulating plant growth, containing an effective amount of a compound of the formula I as set forth in claim 1 and inert additives.

3. A process for regulating the growth of plants, wherein the plants, their habitat and/or their seed are treated with an effective amount of a piperazine-2,3-dione of the formula I as set forth in claim 1.

4. A compound of the formula I as defined in claim 1, wherein $R^1$ and $R^2$ are each $CH_2=CHCH_2$.

5. A compound of the formula I as defined in claim 1, wherein $R^1$ and $R^2$ are each $CH_3$.

6. A compound of the formula I as defined in claim 1, wehrein $R^1$ and $R^2$ are each $i\text{-}C_3H_7$.

7. A compound of the formula I as defined in claim 1, wherein $R^1$ and $R^2$ are each $n\text{-}C_4H_9$.

8. A compound of the formula I as defined in claim 1, wherein $R^1$ and $R^2$ are each $n\text{-}C_5H_{11}$.

9. A compound of the formula * as defined in claim 1, wherein both $R^1$ and $R^2$ are each $CH_2=C(CH_3)CH_2$.

10. A compound of the formula I as defined in claim 1, wherein $R^1$ and $R^2$ are each $H_2=CCH_2$.

* * * * *